United States Patent [19]

Fields et al.

[11] 4,265,879

[45] May 5, 1981

[54] METHOD FOR CONTROLLING BLOOD TRIGLYCERIDES

[75] Inventors: Joseph E. Fields, Ballwin; John H. Johnson, Kirkwood, both of Mo.

[73] Assignee: Monsanto Company, St. Louis, Mo.

[21] Appl. No.: 25,166

[22] Filed: Mar. 29, 1979

Related U.S. Application Data

[63] Continuation of Ser. No. 832,865, Sep. 13, 1977, abandoned, and a continuation-in-part of Ser. No. 572,799, Apr. 29, 1975, Pat. No. 4,117,111, which is a continuation-in-part of Ser. No. 353,832, Apr. 23, 1973, Pat. No. 3,923,972, which is a continuation-in-part of Ser. No. 188,577, Oct. 12, 1971, abandoned, which is a continuation-in-part of Ser. No. 789,081, Jan. 2, 1969, abandoned, said Ser. No. 832,865, is a continuation of Ser. No. 634,723, Nov. 24, 1975, abandoned, which is a continuation-in-part of said Ser. No. 353,832.

[51] Int. Cl.$^3$ .................... A61K 31/74; A61K 31/78
[52] U.S. Cl. ........................................ 424/78; 424/81
[58] Field of Search ................................ 424/78, 81

[56] References Cited

U.S. PATENT DOCUMENTS

| | | | |
|---|---|---|---|
| 3,780,171 | 12/1973 | Irmscher | 424/78 |
| 3,923,972 | 12/1975 | Fields | 424/78 |

FOREIGN PATENT DOCUMENTS 664326  6/1963  Canada ...................... 424/78

OTHER PUBLICATIONS

Webster's Third New Internat. Dict. 1963 p. 1318.
Paoletti, Lipid Pharm., Acd. Press, NY, 1964 pp. 2, 132–136, 381, 382.

*Primary Examiner*—Anna P. Fagelson
*Attorney, Agent, or Firm*—Joseph D. Kennedy; James W. Williams, Jr.

[57] ABSTRACT

The level of blood triglycerides is controlled by administration of polymers of unsaturated carboxylic acids, for example, copolymers of such acids with high molecular weight olefins or vinyl ethers.

16 Claims, No Drawings

METHOD FOR CONTROLLING BLOOD TRIGLYCERIDES

This application is a continuation of Application Ser. No. 832,865, filed Sep. 13, 1977 now abandoned, which is a continuation of Ser. No. 634,723, filed Nov. 24, 1975 now abandoned, which is a continuation-in-part of Ser. No. 353,832, filed Apr. 23, 1973, now U.S. Pat. No. 3,923,972. This application is also a continuation-in-part of application Ser. No. 572,799 filed Apr. 29, 1975, now U.S. Pat. No. 4,117,111, which is a continuation-in-part of said Ser. No. 353,832, which is a continuation-in-part of Ser. No. 188,577 filed Oct. 12, 1971, now abandoned, which in turn is a continuation-in-part of application Ser. No. 789,081, filed Jan. 2, 1969 and now abandoned.

This invention relates to a method for controlling the blood triglyceride levels in a living animal body. The invention is more particularly concerned with controlling or moderating blood cholesterol levels in living animal bodies in need of such control. The link between high levels of triglycerides and cardio-vascular disease in warm blooded vertebrates is well established. High blood levels of triglycerides, along with or independently of high blood levels of blood cholesterol, contributes to cardiovascular disease which is often manifested by chronic high blood pressure and increased risk of incapacitating and often fatal coronary attacks, stroke, etc. Some subjects exhibit both high triglyceride levels and high cholesterol levels, while other subjects exhibit only a high triglyceride level, or only a high cholesterol level. A number of agents have been and are being used for control of blood cholesterol levels, but in general a number of problems are associated with such agents, including patient tolerance and acceptability. Agents for controlling triglycerides are known and in use, but often problems are associated with such agents, including the fact that systemic mechanisms and effects are involved which often produce undesirable side effects. A number of known cholesterol control agents are of little or no value in control of triglyceride levels, and, correspondingly, some agents which are effective in controlling triglyceride levels have little or no effect upon cholesterol levels. There is a need for satisfactory agents to control triglyceride blood levels, either as the only purpose of the agent, or along with control of blood cholesterol levels.

SUMMARY OF THE INVENTION

The present invention is concerned with controlling or moderating blood triglyceride levels in a living animal body in need of such control by orally administering to the living animal body an amount of polymer effective to repress to some extent triglyceride blood levels, the polymer having polymerized unsaturated carboxylic acid or anhydride or derivative components. The invention is particularly concerned with administration of the polymer to control triglyceride levels in subjects faced with a diet containing high levels of fats, but is also concerned with controlling triglyceride levels regardless of the problem necessitating control and even if dietary restrictions are also being used for control purposes.

Other objects and advantages of the present invention will be apparent from the specification and appended claims.

The present invention resides in the discovery that the level of blood triglycerides in a living animal body is lowered by orally administering to said animal body a pharmaceutically effective amount of a polymer selected from the group consisting of (1) a polymerized unsaturated carboxylic acid, or anhydride (2) a copolymer of (a) an unsaturated monomer having, for example, 2 to 30 carbon atoms, and (b) an unsaturated carboxylic acid, anhydride or derivative thereof. By this method the blood triglyceride level in living animal bodies, including warm-blooded vertebrate animals, such as chickens, dogs, rabbits, cats, cattle, swine and primates, for example monkeys, is effectively lowered.

DETAILED DESCRIPTION

The polymer can be orally administered to the living animal body by any suitable means, and in any suitable form. For example, the polymer can be incorporated into ordinary foodstuffs and beverages containing nutritional values in an amount sufficient to produce the desired reduction of blood triglyceride. Also, the polymer can be incorporated into a pharmaceutical composition of the form customarily employed for oral administration. Pharmaceutical compositions containing the polymer may be in liquid form, for example, a solution or suspension specifically adapted for oral administration or in solid form, for example, a tablet, capsule, pill or packaged powder. Advantageously, the pharmaceutical composition containing the polymer can be prepared in unit dosage form using pharmaceutically acceptable carriers, such as, for example, starch, glucose, lactose, gelatin, sucrose, etc. and the like. If desired, the dosage unit can be made up in a sustained release form to give a controlled dosage over an extended period of time.

The amount or dosage of polymer administered to the living animal body will, of course, vary depending among other things, on the size of the living animal body, the particular living animal body to be treated, the level of triglyceride, and the general health of the living animal body, and any pharmaceutically effective amount may be employed. The dosage can be determined with regard to established medical practice. Generally the amount of polymer administered on a daily basis is in the range of from about 0.01 to about 5.0% of the total diet, and typically in the range of from about 0.05 to about 3.0%.

The polymer of use in the present invention may be water soluble or water-insoluble. Many of the normally water-soluble polymers are converted to the water insoluble form by introduction of sufficient crosslinks in the known manner. Crosslinking may be accomplished either during the preparation of the polymer or by subsequent treatment of the polymer to make the polymer insoluble in water. The water insolubility of the polymer can be varied by regulation of the degree of crosslinking of the polymer. The term "water-insoluble" as used herein is taken to mean that the polymer concerned does not dissolve in water or aqueous solutions, even though it may have such characteristics as a high degree of swelling, due to solvation by water even to the extent of existence in a gel form. Such characteristics are typically imparted by crosslinking.

The administration of polymers as described herein will be useful in treatment of subjects in which occasional or chronic high triglyceride blood levels are manifested, or in which such levels would be manifested in the absence of treatment. Thus the polymers can be used to lower the triglyceride blood levels from undesirably high levels, and then the administration can be continued to control or maintain the levels at levels lower than would obtain in the absence of treatment. Or the polymers can be administered for preventive purposes to prevent or retard an increase in triglyceride levels which would occur in the absence of treatment. In general the polymer can be employed to lower triglyceride levels from higher to lower levels, or to lower in the sense of retarding the rate of increase so that the level attained is lower than it would otherwise have been. The polymer can be employed in subjects wherein remedial action is indicated either to correct undesirably high triglyceride levels, or to prevent or lessen their occurrence.

Blood triglyceride levels are known to fluctuate considerably over short time intervals, depending upon proximity to food ingestion times. One of the sources of triglycerides in the blood is dietary fat absorption, and triglycerides from this source will vary widely with food ingestion times. Another source of blood triglycerides in some animals, for example man, is synthesis in the body in organs such as the liver, and triglyceride levels from this source are not closely correlated with food ingestion times; triglycerides from this source are appropriately determined by having the subject fast for a some standard time interval prior to taking a blood sample for triglyceride measurement. For convenience, triglyceride levels thus determined can be referred to as "fasting triglycerides," and levels determined without fasting can be termed "non-fasting triglycerides."

The polymers employed herein have been found useful in lowering, i.e. repressing to some extent, the non-fasting triglycerides. The polymers are also contemplated to be effective in repressing fasting triglycerides and use for such purpose is maintained to be useful and to be within the invention. The fasting triglycerides level has at times been considered to have a more significant relationship to cardio-vascular disease, but there is considerable basis for the view that both fasting and non-fasting triglycerides are significant and it is desirable to avoid excessively high levels of either. Consequently the administration of polymers as taught herein is disclosed as of value for controlling blood triglyceride levels, whether classed as fasting triglycerides, or non-fasting triglycerides, and whether the undesirably high blood triglyceride levels manifested result from synthesis, dietary absorption, or a combination of such sources or other factors. The administration of the polymers can be used to control triglycerides resulting from a steady high fat diet, or occasional atherogenic food ingestion as by a heavy meal, or can be used in conjunction with a restricted non-atherogenic low fat diet to control triglyceride levels.

The triglycerides resulting fairly directly from dietary absorption are generally associated with the lipoprotein blood materials referred to as chylomicrons, which are an extremely low density material. The other lipoprotein fractions associated with triglycerides are the very low density lipoproteins and the low density lipoproteins, the levels of which fluctuate less with diet and apparently result more from synthesis than from absorption. These two classes of materials differ in density, and while both are of low density, yet the materials are of higher density than the chylomicrons. The present invention is intended for using in controlling the chylomicron triglycerides as well as those associated with the other lipoprotein classes, or both.

As previously indicated, the polymers employed in the method of the present invention are (1) polymerized unsaturated carboxylic acids or anhydrides and derivatives, and (2) copolymers of (a) an unsaturated monomer having, for example, 2 to 30 carbon atoms and (b) an unsaturated carboxylic acid anhydride or unsaturated carboxylic acid derivative. The polymers preferably have a weight average molecular weight of at least 1,000 and a degree of polymerization of at least 8.

The polymer may advantageously be an EMA-type polymer.

Among the EMA-type polymers suitable for the practice of the instant invention are polymers and pharmaceutically acceptable salts of polymers having units of the formula

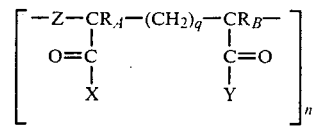

wherein $R_A$ and $R_B$ are selected from the group consisting of hydrogen, halogen (preferably chlorine), alkyl of 1 to 4 carbon atoms (preferably methyl), cyano, phenyl, or mixtures thereof; provided that not more than one of $R_A$ and $R_B$ is phenyl; Z is a bivalent radical (preferably alkylene, phenylalkylene, alkoxyalkylene, alkylcarboxyalkylene and aliphatic acyloxyalkylene) of 1 to 30 carbon atoms, q is zero or one, X and Y are selected from hydroxy, —O alkali metal, OR, —OH—NH$_3$, —OH—R$_3$N, —OH—R$_2$NH, —OH—RNH$_2$, —NRR', —(Q)$_P$—W—(NR'R')$_x$ and —(Q$_P$—W—(—OH)$_x$, wherein x is 1 to 4 and p is zero or one, wherein R is selected from the group consisting of hydrogen, alkyl, phenylalkyl, or phenyl, in each case of 1 to 18 carbon atoms, wherein R' is H or R, wherein Q is oxygen or —NR'—, and wherein W is a bivalent radical preferably selected from alkylene, phenylene, alkylene amine and phenylalkylene having up to 20 carbon atoms, X and Y taken together can be oxygen or —NR—, —N—W(NR'R')$_x$ or —N—W—(NR'R'R")$_x$+ wherein R, W, R' have the meanings previously assigned and R" is alkyl of 1 to 18 carbon atoms, benzyl or aromatic-substituted benzyl. The units of the formula given above are recurring n being at least 8 and can be as much as 100,000 degrees of polymerization. When the units are recurring the symbols in the various recurring units do not necessarily stand for the same thing in all of the recurring units.

Many of these polymers suitable for the practice of the present invention or suitable after conversion to derivatives are commercially available.

The polycarboxylic acid polymers can be of the non-vicinal-type including those containing monomer units, such as acrylic acid, acrylic anhydride, methacrylic acid, crotonic acid or their respective derivatives, including partial salts, amides and esters or of the vicinal type, including maleic, itaconic, citraconic, a-dimethyl maleic, a-butyl maleic, a-phenyl maleic, fumaric, aconitic, a-chloromaleic, a-bromomaleic, a-cyanomaleic acids including their salts, amides and esters. Anhydrides of the foregoing acids are also advantageously employed.

Co-monomers suitable for use with the above polycarboxylic acid monomers include a-olefins, such as ethylene, 2-methyl-pentene-1, propylene, isobutylene, 1- or 2-butene, 1-hexene, 1-octene, 1-decene, 1-dodecene, 1-octadecene, and other vinyl monomers, such as styrene, a-methyl styrene, vinyltoluene, vinyl acetate, vinyl chloride, vinyl formate, vinyl alkyl ethers, e.g. methyl-vinylether, alkyl acrylates, alkyl methacrylates, acrylamides, methacrylamides, alkylmethacrylamides and alkylacrylamides, or mixtures of these monomers. Reactivity of some functional groups in the copolymers resulting from some of these monomers permits formation of other useful functional groups in the formed copolymer, including hydroxy, lactone, amine and lactam groups.

Any of the said carboxylic acids or derivatives, may be copolymerized with any of the other monomers described above, and any other monomer which forms a copolymer with carboxylic acids or derivatives. Although these copolymers can be prepared by direct polymerization of the various monomers, frequently they are more easily prepared by an after-reaction modification of an existing copolymer. Copolymers are conveniently identified in terms of their monomeric constituents. The names so applied refer to the molecular structure and are not limited to the polymers prepared by the copolymerization of the specified monomers.

The initial copolymers of anhydrides and another monomer can be converted to carboxyl-containing copolymers by reaction with water, and to ammonium, alkali and alkaline earth metal and alkylamine salts thereof by reaction with alkali metal compounds, alkaline earth metal compounds, amines or ammonia. Other suitable derivatives of the above polymers include the alkyl or other esters and amides, alkyl amides, dialkyl amides, phenylalkyl amides or phenyl amides prepared by reacting carboxyl groups on the polymer chain with the selected amines or alkyl or phenylalkyl alcohol, as well as amino esters, amino amides, hydroxy amides and hydroxy esters, wherein the functional groups are separated by alkylene, phenyl, alkylene amine, alkylene oxide, phenylalkyl, phenylalkylphenyl, or alkylphenylalkyl or other aryl groups. Moieties bearing amine or amine salts including quaternary salt groups are conveniently formed by reaction of the carboxyls of their anhydride precursors, where applicable with polyfunctional amines such as dimethylaminopropylamine or dialkylamino-alcohols such as dimethylaminoethanol, the former forming an amide linkage with the polymer, or in certain cases at higher temperatures forming an imide linkage with vicinal carboxyls, and the latter forming an ester linkage. Such pendant free amine groups can then be converted, if desired, to their simple or quaternary salts.

Polymers of the above type include the following classes of polymers, and their derivatives: ethylene/maleic anhydride copolymers, isobutylene/maleic anhydride copolymer, 2-methyl-pentene-1/maleic anhydride copolymers, styrene/maleic anhydride copolymers, vinylacetate/maleic anhydride copolymers, a-methylstyrene/maleic anhydride copolymers, polymaleic anhydride polymers, polyacrylic anhydride polymers, polyacrylic acid polymers, octadene-1/maleic anhydride copolymers, lowerlalkylaminoloweralkylimide of octadecene-1/maleic anhydride copolymers, aliphatic ester of ethylene/maleic anhydride copolymers, vinylalkylether/maleic anhydride copolymers, aliphatic methacrylate/methacrylamide copolymers, aliphatic methacrylate/diloweralkyl-aminoloweralkyl methacrylate copolymers, lowerlalkylamino-loweralkylimide of styrene maleic anhydride copolymers and polymethacrylic acid polymers.

Individual examples of such polymers include ethylene/maleic anhydride copolymer, the disodium salt of isobutylene/maleic anhydride copolymer, the calcium salt of styrene/maleic anhydride copolymer, the monopotassium salt of divinylether/maleic anhydride copolymer, hydrolyzed vinyl methyl ether/citraconic anhydride copolymer, octadecene-1/maleic anhydride copolymer, ethylene/maleic acid copolymer, the dipotassium salt of isobutylene/maleic acid copolymer, the half amide half ammonium salt of isobutylene/maleic anhydride copolymer, ethylene/acrylic acid copolymer, ethylene/acrylic anhydride copolymer, half capryl ester of hexene-1/acrylic anhydride copolymer, ethylene/aconitic anhydride copolymer, half ethylamide of styrene/maleic anhydride copolymer, ethylene/fumaric acid copolymer, octylamide acid of ethylene/maleic anhydride copolymer, octadecylamide ammonium salt of vinylmethylether/maleic anhydride copolymer, dimethylaminopropylamide acid of divinylether/maleic anhydride copolymer, isobutylamide of vinyl acetate/maleic anhydride copolymer, methiodide quaternary derivative of N,N-dimethylaminoethylamide of polymaleic anhydride, octadecyl ester ammonium salt of ethylene/itaconic anhydride copolymers, butylamine half amide of hexene-1/chloromaleic anhydride copolymer, the partial diamide of ethylene/maleic anhydride copolymer, n-decylamide of decene-1/maleic anhydride copolymer, n-decylamide of decene-1/maleic anhydride copolymer, N,N-diethylaminopropylamide ammonium salt of isobutylene/maleic anhydride copolymer, dimethyl sulfate quaternary salt of dimethylaminoethylamide of polymaleic anhydride, the partial half hexylamide of vinylethylether/maleic anhydride copolymer, the diammonium salt of ethylene/maleic anhydride copolymer, the monoamide acid of propylene/maleic anhydride copolymer, N-ethyl monoamide of divinylether/maleic anhydride copolymer, N-dodecyl monoamide of vinylmethylether/maleic anhydride copolymer, N,N-dimethylaminopropylimide of triacontene/maleic anhydride copolymer, N,N-dimethylaminopropyl monoamide of styrene/citraconic anhydride copolymer, n-butylmonoamide of polymaleic anhydride, N,N-diethylmonoamide ammonium salt of vinyl acetate/maleic anhydride copolymer, n-butylimide of ethylene/maleic anhydride copolymer, octadecylimide of polymaleic anhydride, N,N-dimethylaminopropylimide of styrene/maleic anhydride copolymer, dimethylsulfate quaternary salt of diethylaminopropylimide of divinylether/maleic anhydride copolymer, N,N-dimethylaminopropyl half amide of paramethyl styrene/maleic anhydride copolymer, methyliodide quaternary salt of dimethylaminohexyl half amide half ammonium salt of a-methylstyrene/maleic anhydride copolymer, N,N-diethylaminoethyl half amide half sodium salt of isobutylene/maleic anhydride copolymer, partial lauryl ester of ethylene/maleic anhydride copolymer, vinyl octadecyl ether/maleic anhydride copolymer, stearyl methacrylate/methacrylamide copolymer and stearyl methacrylate/N,N-dimethylaminoethyl methacrylate copolymer.

A particularly preferred class of polymers for use in the present invention are lipophilic polymers, that is, polymers which have a lipophilic grouping or groupings included therein. A lipophilic grouping or moiety typically contains 6 or more atom units and may be in any suitable form such as a polyalkylene or alkylene oxide containing 6 or more atom units or as an ester, amide or imide unit containing 6 or more atom units, for example, 6 to 30 carbon atoms formed by reaction of the carboxyl containing monomer with lipohilic amines or alcohols such as, for example, hexanol, octanol, octylamine, hexylamine, octadecanol, etc. and the like. Examples of such preferred polymers include the octadecylimide of polymaleic anhydride, the methyl iodide quaternary salt of dimethylaminohexyl half amide half ammonium salt of a-methylstyrene/maleic anhydride copolymer, dodecyl monoamide of vinylmethylether/maleic anhydride copolymer, the octadecyl ester ammonium salt of ethylene/itaconic anhydride copolymer, the decylamide of decene-1/maleic anhydride copolymer, octadecene-1/maleic anhydride copolymer etc. and the like.

Pharmaceutically acceptable alkaline earth metals and alkali metals, such as calcium, magnesium and potassium are useful in preparing conveniently administered forms of the polyelectrolyte polymers of this invention. The salts of metals such as magnesium, aluminum, zinc, iron, barium and bismuth are also useful in the present invention.

Representative EMA-type carboxylic acid or anhydrideolefin polymers, especially maleic acid or anhydride-olefin polymers of the foregoing type are known, for example, from U.S. Pat. Nos. 2,378,629; 2,396,785; 3,157,595; and 3,340,680. Generally, the copolymers are prepared by reacting ethylene or other unsaturated monomer, or mixtures thereof, with the acid anhydride in the presence of a peroxide catalyst in an aliphatic or aromatic hydrocarbon solvent for the monomers but non-solvent for the interpolymer formed. Suitable solvents include benzene, toluene, xylene, chlorinated benzene and the like. While benzoyl peroxide is usually the preferred catalyst, other peroxides such as acetyl peroxide, butyryl peroxide, ditertiary butyl peroxide, lauroyl peroxide and the like, or any of the numerous azo catalysts, are satisfactory since they are soluble in organic solvents. The copolymer typically contains from about 25 to about 75% (mole %) of the olefin and preferably contains substantially equimolar quantities of the olefin residue and the anhydride or acid residue; that is, a mole ratio of olefin to anhydride or acid in the range of from about 2:3 to about 3:2. Generally, the copolymer will have a degree of polymerization of 8 to 100,000 preferably about 100 to 5,000, and a molecular weight of about 1,000 to 1,000,000, preferably about 10,000 to 500,000. The properties of the polymer, such as molecular weight, for example, are regulated by proper choice of the catalyst and control of one or more of the variables such as ratio of reactants, temperature, and catalyst concentration or the addition of regulating chain transfer agents, such as diisopropyl benzene, propionic acid, alkyl aldehydes, or the like. Numerous of these polymers are commercially available.

Derivatives containing basic or cationic groups can be prepared by any convenient procedure. Representative derivatives of polymers employed in the present invention are known to the art, for example, from U.S. Pat. No. 3,398,092. One group of useful derivatives are those in which the carboxyl groups are partially replaced with basic or cationic bearing moieties. For example, useful derivatives are conveniently formed by reaction of the carboxyls with polyfunctional amines such as dimethylaminopropylamine or dialkylamino alcohols such as dimethylaminoethanol, the former forming an amide linkage with the polymer, or in certain cases at higher temperatures forming an imide linkage with the vicinal carboxyls and the latter forming an ester linkage. Such pendant free amine groups can then be converted, if desired, to their simple or quaternary salts.

Imides of a starting carboxyl or carboxylic acid anhydride containing polymer, e.g. EMA, are produced by:

(A) Heating a limiting amount of a secondary or tertiary aminolowerlalkylamine with the anhydride or carboxyl-containing form of the polymer in a suitable solvent (e.g. Xylene) at a temperature of about 140°–150° C. until water is no longer given off. Such a reaction simultaneously results in formation of imide groups in proportion to the amount of amine added and in the reformation of anhydride groups for the remainder of the polymer units. In this manner, imide-polymer products are formed which possess imide linkages, the remaining carboxyl groups, when present, being in the anhydride form.

(B) Alternatively, a partial amide polymer product may be converted to the partial imide polymer product by heating a partial amide-polymer product in vacuo at 140°–150° C. until water is no longer given off. Such an imide polymer product likewise possesses comparable proportions of imide and anhydride groups depending upon the number of amide groups originally contained in the starting partial amide-polymer product.

Partial secondary or tertiary aminolowerlakylamides of the starting carboxyl or carboxylic acid anhydride-containig polymer, e.g., EMA, are obtained by contacting the polymer with a limiting amount of the selected amine in suspension in a solvent such as benzene or hexane, resulting in formation of a partial amide-acid-anhydride derivative of the polymer, or a corresponding amide-carboxylic derivative thereof. The number of amide groups is dependent upon the quantity of the amine used as compared with the quantity of polymer employed.

Partial aminoester-polymer products are most conveniently prepared by heating at reflux temperatures overnight a limiting quantity of the selected aminoalcohol and carboxyl or carboxylic acid anhydride containing polymer, e.g. EMA, in a dry organic solvent such as toluene or dimethylformamide and with the optional use of an acidic or basic catalyst such as p-toluenesulfonic acid or sodium alkoxide. The resulting product contains ester groups, carboxylic acid groups and anhydride groups, the respective numbers of which are determined by the quantity of aminoalcohol used in the reaction compared to the amount of polymer employed and, in some cases, by the temperature at which the reaction is carried out.

Suitable blocking and unblocking of the amine moiety of the reactant employed in preparing amides, esters or imides may be effected when required. Residual, non-modified, polymer units may optionally be converted to neutral groups or units by attachment to the polymer molecule of compounds including alkylamines, aminoalcohols, and alcohols.

Alternatively, the cationic character of the polymer can be provided through incorporation of monomers which impart a basic or cationic character such as C-vinyl pyridines, vinyl amine, the several amino-substituted vinyl benzenes (or toluenes, etc.), amine-bearing acrylates (or methacrylates, etc.), vinyl imidazole, etc.

The invention will be understood more fully by reference to the following specific examples. It is understood that the examples are presented for the purpose of illustration only and are not intended as a limitation of the invention.

The polymers utilized herein have particular functional characteristics which are apparently responsible for effectiveness. The polymers are believed to be effective, at least in part, because of ability to interfere with fat breakdown and transportation and absorption of fat and related materials. The useful polymers in general have surfactant characteristics, and can be termed polymeric surfactants, with the term "surfactant" referring to materials having a tendency to concentrate at the surface of an aqueous solution and to alter its surface properties. Surfactants in general have hydrophilic groups, and this appears to be true of the polymeric surfactants utilized herein. The polymers utilized usually have some hydrocarbon or similar moiety, and a hydrophilic carboxyl group or derivative. It appears that the efficiency of the polymers is affected by the size and character of the hydrophobic groups, and that groups attracted to fats will contribute to the efficiency of the polymers for controlling triglycerides. Such lipophilic groups often have chains similar in length or properties to those in natural fats, and can have, for example, hydrocarbon chains of from 6 or 8 or so carbon atoms up to 22 or 24 or more carbon atoms. A more preferred range is from about 10 to about 18 or 20 carbon atoms. In the event oxygen or other hetero atoms are included, as from polymerization of a vinyl ether, the chain lengths may vary somewhat but can be selected to have characteristics like the aforesaid hydrocarbon chains. In general herein for simplicity no distinction will be made between the appropriate number of atoms in hydrocarbon chains as compared to other hydrophobic groups, but it will be understood that it is intended that other hydrophobic groups be those of characteristics of straight chain hydrocarbons of the specified atom ranges. In determining chain lenghts herein, the atoms are conveniently counted in terms of the total number of atoms in a monomer, without regard to the particular position of the monomer in the polymer, particularly when an alpha-olefin hydrocarbon is used, e.g. octadecene contributes an 18 carbon atom grouping to the polymer. There generally is no reason to use hydrophobic groupings with more than the suggested range of carbon atoms and such often are not readily available, but groupings of appropriate lipophilic character can be used containing up to 30 or more carbon atoms. As stated, lipophilic character apparently contributes to the effectiveness of the polymers and therefore lipophilic polymers will ordinarily be used. There is some indication that groupings tend to decline in or lose lipophilic character as extremely long chain lengths are reached and it may be advisable to avoid such if the advantages of lipophilic character are to prevail. Polymers from higher molecular weight olefins trend toward a waxy character as molecular weight is increased, in contrast to the non-waxy character of polymers from lower molecular weight range olefins.

The polymeric surfactants used herein contain hydrophilic groups which are generally the carboxyl group or a derivative thereof. Appropriate hydrophilic character in use can be supplied by using polymers with free carboxyl or carboxyl groups, or anhydride groups, so frequently such groups are utilized along with other partial derivative groups. However polymeric surfactants having various carboxyl derivatives as discussed herein can be used. The carboxyl group can, of course, also be utilized to introduce other hydrophobic groups, as by esterification with a long hydrocarbon chain alcohol wherein the hydrocarbon chain supplies hydrophobic character, and partial esters of carboxyl containing polymers described herein can be used in such embodiment or otherwise.

Further description of polymers considered suitable for use herein includes copolymers of vinyl ether with maleic acid or anhydride or appropriate derivatives, e.g. vinyl alkyl ethers with 8, 10, 12, 16 or 18 carbon atoms in the alkyl group, copolymers of vinyl ether with other unsaturated acids or appropriate derivatives, e.g. of acrylic acid, methacrylic acid, aconitic acid, itaconic acid, crotonic acid or citroconic acid, with for example the number of carbon atoms in the vinyl ether as stated for the maleic copolymers, with an alkyl of 12 carbon atoms being a convenient choice from a range of 8 to 20 or so; copolymers of olefinic hydrocarbons, such as of about 8 or 10 to about 18 or 22 carbon atoms with acrylic or methacrylic acids, although it may be necessary to use some special expedients to obtain such polymers, such as copolymerization of the olefin with acrylamide, followed by hydrolysis; copolymers of vinyl esters with unsaturated carboxylic acids, e.g. maleic acid or anhydride, acrylic acid, aconitic acid, itaconic acid, crotonic acid, citraconic acid, etc., with the ester carboxylate moiety having a number of carbon atoms in the range stated above for alkyl groups in copolymers of vinyl ethers with such acids, with vinyl esters of a C-12 carboxylic acid, or vinyl stearate being convenient choices; and long chain partial esters of the afore-named unsaturated carboxylic acids, with the esterifying groups having a number of carbon atoms as in the aforementioned alkyl groups, e.g. stearyl methacrylate/methacrylic acid copolymer, stearyl acrylate/acrylic acid copolymer, or such variations as stearyl methacrylate/acrylic acid copolymer and the partial lauryl ester of ethylene/maleic acid copolymer.

EXAMPLE 1

A test program was conducted with 180 rabbits, randomly divided into 10 rabbits per test group and caged in pairs. The rabbits were virgin female New Zealand white rabbits weighing 3-4 lbs. The rabbits were fed a standard rabbit chow. (Ralston Purina) for a two-week conditioning period. At the beginning of the third week, the rabbits (except for a nonatherogenic standard chow control group) were fed an atherogenic diet which was the standard chow to which 2% tallow, 0.2% cholesterol, and 1% non-nutritive filler (Solka Floc) had been added. At the beginning of the fifth week, the filler was replaced with 1% of the test material, except for an atherogenic diet control group. The test materials were designated alpha-olefin/maleic anhydride copolymers, as such or hyrolyzed, or designated vinyl ether/maleic anhydride copolymers, as such or hydrolyzed, or Cholestyramine hypercholesteremic drug, a corss-linked divinyl benzene polystyrene ion exchange resin containing quaternary ammonium groups, commercially available under the trade name Questran for treating hypercholesteremia, all as reported below. Blood samples (ear vein) were taken weekly, starting with the end of the second week, and continuing through the end of the tenth week, and sent to Midwest Research Laboratories for analysis for serum triglycerides.

Average values were calculated and are reported in Table 1 below. The values for the second through fifth weeks, during which all rabbits were on the same diet (except for those kept on standard chow) are reported as pre-test values. With the test material being added at the end of the fifth week, that is the start of the test period, and results are reported for 1 to 5 weeks post additive. Overall average triglyceride values for the rabbits at the start of test period were around 60–70 mg%, and with most groups was about the same as or slightly lower than during the conditioning period. From that point on triglyceride values of the atherogenic control group stayed at a relatively high level, while those on the standard control showed a decrease, presumably due to increased age of the rabbits.

From the data in Table 1 it can be seen that administration of the test compounds of this invention in general results in lower triglyceride values than obtained in the atherogenic control group, with the 5-week values being lower in all cases, except for the $C_{24-28}$ olefin compound, which apparently was not effective in the dosage used.

resulted in some lowering of the slope compared to the atherogenic control group, and that some even showed sufficient control of triglycerides in rabbits on a highly atherogenic diet to show a nearly level or downward trend approximating that of the control group on a standard diet. Comparing the final 5-week post additive results similarly shows that administration of test compounds lowered the triglyceride levels to values lower than that of the atherogenic control group. Thus in every case the values were lower than they would have been in the absence of treatment and the compounds were demonstrated effective in controlling triglyceride levels. Some of the compounds were so effective that they controlled the triglyceride values to approximately what they would have been for rabbits on a normal diet, despite the highly atherogenic diet which the rabbits were on. With a number of compounds, the 5-week values were actually numerically lower than the start-

TABLE 1

| | Triglycerides (mg %) Weeks | | | | | | | | |
|---|---|---|---|---|---|---|---|---|---|
| | Pre-test | | | | Post Additive | | | | |
| Test Material | 2nd | 3rd | 4th | 5th | 1 | 2 | 3 | 4 | 5 |
| Control (Standard) | 85 | 80 | — | 62 | 25 | 48 | 25 | 40 | 40 |
| Control (Atherogenic) | 131 | 90 | 83 | 120 | 85 | 74 | 115 | 165 | 120 |
| Cholestyramine | 90 | — | — | 115 | 90 | 115 | 140 | 190 | 275 |
| Decene/maleic anhydride | — | — | — | 40 | 74 | 48 | 39 | 48 | 45 |
| Decene/maleic acid | 66 | — | — | 70 | 46 | 69 | 65 | 99 | 90 |
| Tetradecene/maleic anhydride | 60 | — | — | 45 | 65 | 60 | 70 | 65 | 45 |
| Tetradecene/maleic acid | 90 | — | — | 61 | 66 | 50 | 45 | 50 | 66 |
| Octadecene/maleic anhydride | 65 | — | — | 65 | 65 | 70 | 70 | 85 | 85 |
| Octadecene/maleic acid | 85 | — | — | 75 | 70 | 60 | 35 | 45 | 60 |
| $C_{20-24}$ olefin/maleic anhydride | 85 | — | — | 90 | 85 | 60 | 60 | 95 | 90 |
| $C_{20-24}$ olefin/maleic acid | 89 | — | — | 70 | 63 | 70 | 50 | 73 | 50 |
| $C_{24-28}$ olefin/maleic anhydride | 85 | — | — | 70 | — | 95 | 90 | 145 | 145 |
| $C_{24-28}$ olefin/maleic acid | 65 | — | — | 55 | 95 | 110 | 125 | 135 | 126 |
| Dodecyl vinyl ether/maleic anhydride | — | — | — | 54 | — | 50 | — | 65 | 48 |
| Dodecyl vinyl ether/maleic acid | — | — | — | 107 | 85 | 60 | 60 | — | 51 |
| Octadecyl vinyl ether/maleic anhydride | — | — | — | 60 | — | 29 | — | 53 | 28 |
| Octadecyl vinyl ether/maleic acid | 74 | — | — | 55 | 35 | 75 | 44 | 50 | 49 |

To illustrate the trend of the data during the test period, the values for 1 to 5 week values from Table 1 were placed on graph paper and smooth curves were traced based on such points. In Table 2 below the values from such curves at 1 and 5 weeks are given.

TABLE 2

| | Triglycerides (mg%) Week (Post Additive) | |
|---|---|---|
| Test Material | 1 | 5 |
| Control (Standard) | 55 | 40 |
| Control (Atherogenic) | 77 | 140 |
| Cholestyramine | 90 | 275 |
| Decene/maleic anhydride | 60 | 45 |
| Decene/maleic acid | 45 | 105 |
| Tetradecene/maleic anhydride | 68 | 52 |
| Tetradecene/maleic acid | 56 | 45 |
| Octadecene/maleic anhydride | 65 | 89 |
| Octadecene/maleic acid | 65 | 50 |
| $C_{20-24}$ olefin/maleic anhydride | 75 | 78 |
| $C_{20-24}$ olefin/maleic acid | 68 | 60 |
| Dodecyl vinyl ether/maleic anhydride | 58 | 54 |
| Dodecyl vinyl ether/maleic acid | 85 | 50 |
| Octadecyl vinyl ether/maleic acid | 52 | 58 |

By a comparison of the 1-week and 5-week values in Table 2, it can be seen that all of the test compounds ing values.

It is of further interest that a recognized cholesterol control agent, Cholestyramine, not only failed to control triglycerides in the test, but actually caused an increase in triglyceride levels.

It will be noted that both the anhydride and acid (hydrolyzed) forms are demonstrated effective in controlling triglycerides, with the anhydride tending to be better with shorter chain olefin moieties, while the acid tends to be better with longer chain olefin moieties. It appears that similar results can be obtained with salt, ester, amide and other derivatives, in view of the surfactant properties of such polymers as discussed herein, and in view of the correlation of other physiological effects of such derivatives with those of the acid and anhydride. Similarly it is maintained that the polymers described hereinabove in the further description of polymers can be employed in the above tests and demonstrated effective in controlling triglycerides.

EXAMPLE 2

This example shows the effectiveness of octadecene-1/maleic anhydride (substantially equimolar copolymer) in the method of the present invention. Forty New Zealand white rabbits weighing an average of 2600 grams each were divided into five groups of equal number. The groups were fed *ad libitum* for five weeks a high cholesterol diet. The first group (control) was fed Purina Rabbit Chow brand rabbit feed supplemented with 2% animal tallow, 1% cellulose and 0.2% cholesterol. The second group was fed the identical feed as the control with the exception that 0.5% octadecene-maleic anhydride was substituted for 0.5% of the cellulose. The third group was fed the identical feed as the control with the exception that 1% octadecene maleic anhydride was substituted for the 1% cellulose. The fourth group was fed the identical feed as the control with the exception that 0.5% CHOLESTYRAMINE was substituted for 0.5% of the cellulose. The fifth group was fed the identical feed as the control with the exception that 1% CHOLESTYRAMINE was substituted for the 1% cellulose. Feces were collected during the final day of the test. On completion of the five-week feeding period the animals were sacrificed. The measurements performed in Example 1 above were carried out. Fecal fat was also measured. The measurements were averaged and are presented in Table 3. They illustrate the ability of 1% octadecene/maleic anhydride copolymer in the atherogenic diet to maintain lowered triglyceride levels.

Among the polymers effective for controlling triglycerides as taught herein, types of polymers which have been particularly used as exemplifications and demonstrated effective are (1) a group of polymers which are copolymers of higher α-olefins (10–22 carbon atoms or more) and maleic acid or maleic anhydride and (2) a group of polymers which are copolymers of higher alkyl vinyl ethers (10–22 carbon atoms or more) and maleic acid or maleic anhydride.

TABLE 3

|  |  | PLASMA | | LIVER | | FECES |
| --- | --- | --- | --- | --- | --- | --- |
|  |  | Cholesterol *mg % | Triglyceride *mg % | Cholesterol % of wet weight | Fat | Fat % of dry wt. |
| Group 1 | (Control) | 672 | 106 | .92 | 7.80 | 4.51 |
| Group 2 | (0.5% Octadecene-maleic anhydride) | 186 | 113 | .47 | 5.98 | 6.03 |
| Group 3 | (1.0% Octadecene-maleic anhydride) | 89 | 56 | .41 | 5.80 | 6.29 |
| Group 4 | (0.5% CHOLESTYRAMINE) | 356 | 68 | .79 | 7.36 | 7.12 |
| Group 5 | (1.0% CHOLESTYRAMINE) | 310 | 105 | .74 | 7.18 | 6.04 |

*mg per 100 cc of plasma.

The polymers utilized herein will generally be in molecular weight ranges obtainable by conventional polymerization procedures which may range up to relatively high molecular weights of 1,000,000 and above, but high molecular weight polymers can be employed regardless of how high the molecular weight.

EXAMPLE 3

Sprague-Dawley female rats (180–200 grams) were obtained and conditioned to cages in a controlled temperature room with light cycling (on at 3:00 p.m. and off at 3:00 a.m.). Rats were fed a standard ground chow during the conditioning period. The rats were divided into three groups (about 16 per group). For a non-atherogenic diet, the chow was used without additives and fed to one group. For an atherogenic diet, 10 grams corn oil and 1 gram cholesterol was added to 100 grams chow, and this was fed to groups two and three. However, in the diet for the third group, 2 grams of test polymer (per 100 grams chow) was added after two weeks on the atherogenic diet. To obtain blood samples, rats (group of 6–10) were sacrificed at the mid-dark phase of the cycle (about 9:00 a.m.). The triglyceride and cholesterol values are as reported below. The test polymer employed was a hydrolyzed octadecene-1/maleic anhydride copolymer, which was primarily in the acid form.

|  | Fourth Week | |
| --- | --- | --- |
|  | Triglycerides (mg %) | Cholesterol (mg %) |
| 1. Standard Chow | 81 | 59 |
| 2. Antherogenic Diet | 131 | 83 |
| 3. Atherogenic Diet + octadecene/maleic (after 2 weeks) | 92 | 64 |

It can be seen that the addition of the higher olefin/maleic copolymer caused a lowering of the triglyceride value as compared to the control.

It is contemplated that the present invention will provide a treatment of value in controlling triglyceride levels in subjects with hypertriglyceridemia, or type IIb, type III and type IV hyperlipoproteinemia. It will be noted that some cholesterol control agents, for example Cholestyramine, appear to raise triglyceride levels and increase fat excretion, with some variances, due to conditions, type of lipoprotein, etc., while the present agents apparently increase fat excretion and lower both triglyceride and cholesterol levels. For reports on Cholestyramine effects, see Jones et al, Journal Laboratory and Clinical Medicine, Vol. 75, June 1970, pp. 953 to 966; Hackins et al, Proceedings of Society Experimental Medical Biology, Vol. 118, pages 399–402, (1965); Weizel et al Proceedings of Society Experimental Medical Biology, Vol. 130, pages 149–150; Physicians Desk Reference, 1974 (Medical Economics) pages 986–987.

Representative formulations embodying polymers within the scope of the present invention are:

TABLET FORMULATION

The following formulation provides for the manufacture of 1,000 tablets:

|  |  | GRAMS |
| --- | --- | --- |
| (1) | Octadecene-1/maleic anhydride copolymer | 25 |
| (2) | Lactose | 181 |
| (3) | Corn Starch | 92 |
| (4) | Magnesium Stearate | 2 |

Thoroughly granulate a mixture of 72 grams of cornstarch and the lactose with a paste prepared by dissolving 20 grams of cornstarch in 100 ml of hot distilled water. Dry the resulting granulation at 40°–45° C. and pass it through a No. 16-mesh screen. To the dried, screened granulation add a blended mixture of the active ingredient (1) and the magnesium stearate. Thoroughly blend and then press into tablets of 300 mg. each.

CAPSULE FORMULATION

The following formulation provides for the manufacture of 1,000 capsules:

|     |                                                                            | GRAMS |
| --- | -------------------------------------------------------------------------- | ----- |
| (1) | N,N-dimethylaminopropylimide of octadecene-1/maleic anhydride copolymer    | 25    |
| (2) | Lactose                                                                    | 274   |
| (3) | Magnesium Stearate                                                         | 2     |

Mix active ingredient (1) with the lactose and blend in the magnesium stearate. Fill hard gela capsules with 300 mg. each of the blended mixture to produce capsules containing the active ingredient.

The present invention provides pharmaceutical compositions containing the described polymers and pharmaceutically acceptable carriers therefore. Thus any of the polymers disclosed as effective herein, either generically or specifically, can be combined with carriers and used for administration in convenient dosage forms. Such pharmaceutical composition can include various carriers and additives as disclosed herein and can include various sweetening or flavoring agents to improve palatability. Also appropriate purification or sterilization procedures can be employed to provide a potable or sterile pharmaceutical composition fit for human consumption. The preparation procedures can include polymer isolation and purification procedures to insure standard uniform composition and physical form within specified tolerances in order to provide uniform quality, strength, effectiveness and other properties, as well as procedures to insure food grade purity.

The administration of the various unsaturated acid, anhydride and derivative polymers and copolymers as taught herein is advantageous in providing a method of controlling blood triglyceride levels in animal bodies in need of such control but not in need of control of cholesterol levels, for example not having elevated but rather cholesterol levels in normal range, and also providing a method of controlling both triglyceride and cholesterol levels in an animal body in need of controlling both.

The polymers utilized in the present invention are non-sytemic, i.e. they apparently are effective in the gastrointestinal tract and are not appreciably absorbed through the intestinal wall into the blood stream. The essentially non-systemic nature is considered advantageous in that it lessens the possibilities for unnecessary interference with body processes and functions and potential side effects. Purification procedures can be used to remove low molecular weight polymer or residual monomer fractions which conceivably may have a greater tendency toward absorption.

The polymers taught herein for administration in accordance with the present invention can be utilized as such, or combined with carriers, adjuvants or comestibles as in pharmaceutical compositions, foodstuffs, animal feeds, and the like.

While the invention has been described with reference to particular embodiments thereof, it will be appreciated that modifications and variations are possible without departing from the invention.

What is claimed is:

1. A method for controlling the blood triglyceride level in a living animal body in need thereof comprising orally administering to said animal body a pharmaceutically effective amount for such purpose of a non-systemic copolymer of (1) an alpha alkene of about 10 to about 22 carbon atoms and (2) maleic acid or anhydride, or a pharmaceutically acceptable amide, ester, imide, salt thereof or mixtures thereof, said copolymer having a molecular weight in the range of from about 1,000 to 1,000,000.

2. The method of claim 1 wherein the copolymer is octadecene-1/maleic anhydride.

3. The method of claim 1 wherein the copolymer is decene-1/maleic anhydride.

4. The method of claim 1 wherein the copolymer is octadecene-1/maleic acid.

5. The method of claim 1 in which the copolymer is a lipophilic copolymer of an alpha-alkene of 10 to 22 carbon atoms and maleic acid or anhydride.

6. The method of claim 1 in which the copolymer is a polyelectrolyte copolymer of an alkene of 10 to 22 carbon atoms.

7. The method of claim 1 in which the alkene has 10 to 18 carbon atoms.

8. The method of claim 1 in which the maleic component of the copolymer is a mixture of the recited maleic components.

9. The method of claim 1 in which the copolymer is a copolymer of maleic acid or anhydride.

10. The method of claim 1 further defined in that the control is achieved by interfering with fat absorption.

11. The method of claim 1 in which non-fasting triglyceride levels in the animal body are in need of control.

12. The method of claim 1 in which fasting triglyceride levels in the animal body are in need of control.

13. The method of claim 1 in which a low fat diet is used for control along with oral administration of said copolymer.

14. The method of claim 1 in which the animal body is on an atherogenic diet.

15. The method of claim 1 in which the triglycerides are controlled to values near that obtainable by a normal low fat diet.

16. The method of claim 1 in which the living animal body does not have an elevated cholesterol level.

* * * * *